United States Patent
Grady et al.

(10) Patent No.: US 8,373,008 B2
(45) Date of Patent: Feb. 12, 2013

(54) RECOVERY OF BUTANOL FROM A MIXTURE OF BUTANOL, WATER, AND AN ORGANIC EXTRACTANT

(75) Inventors: Michael Charles Grady, Oaklyn, NJ (US); William D. Parten, Wilmington, DE (US); Bruce Vrana, Hockessin, DE (US); Yihui Tom Xu, Newark, DE (US); Joseph J. Zaher, Newark, DE (US)

(73) Assignee: Butamax (TM) Advanced Biofuels LLC, Wilmington, DE (US)

( * ) Notice: Subject to any disclaimer, the term of this patent is extended or adjusted under 35 U.S.C. 154(b) by 33 days.

(21) Appl. No.: 12/948,945

(22) Filed: Nov. 18, 2010

(65) Prior Publication Data

US 2011/0288344 A1 Nov. 24, 2011

Related U.S. Application Data

(60) Provisional application No. 61/263,509, filed on Nov. 23, 2009.

(51) Int. Cl.
*C07C 29/80* (2006.01)
*C07C 29/84* (2006.01)

(52) U.S. Cl. ........................................ 568/913; 568/918
(58) Field of Classification Search .................. 568/913, 568/918
See application file for complete search history.

(56) References Cited

U.S. PATENT DOCUMENTS

2007/0092957 A1 4/2007 Donaldson et al.
2009/0305370 A1 12/2009 Grady et al.
2011/0097773 A1 4/2011 Grady et al.

FOREIGN PATENT DOCUMENTS

WO 2009149270 12/2009

OTHER PUBLICATIONS

Ezeji et al., "Bioproduction of butanol from biomass: from genes to bioreactors", Current Opinion in Biotechnology, London, GB, vol. 18, No. 3, Jun. 8, 2007, pp. 220-227.
International Search Report and Written Opinion for corresponding PCT/US2010/057597 mailed May 4, 2011.
U.S. Appl. No. 12/834,915, filed Jul. 13, 2010.
U.S. Appl. No. 12/834,916, filed Jul. 13, 2010.

*Primary Examiner* — Elvis O Price
(74) *Attorney, Agent, or Firm* — Christine M. Lhulier (57) ABSTRACT

A process for recovering butanol from a mixture comprising a water-immiscible organic extractant, water, butanol, and optionally a non-condensable gas, is provided. The butanol is selected from 1-butanol, 2-butanol, isobutanol, and mixtures thereof. An overhead stream from a first distillation column is condensed to recover a mixed condensate. An entrainer is added to at least one appropriate process stream or vessel such that the mixed condensate comprises sufficient entrainer to provide phase separation of the organic and the aqueous phases to provide for recovery of the butanol.

23 Claims, 2 Drawing Sheets

RECOVERY OF BUTANOL FROM A MIXTURE OF BUTANOL, WATER, AND AN ORGANIC EXTRACTANT

CROSS-REFERENCE TO RELATED CASES

This application claims the benefit of priority to U.S. Provisional Patent Application Ser. No. 61/263,509, filed on Nov. 23, 2009, the entirety of which is herein incorporated by reference.

FIELD OF THE INVENTION

Processes for recovering butanol from a butanol-containing organic phase obtained from an extractive fermentation process are provided. Specifically, processes for separating butanol from a mixture comprising butanol, water, a water-immiscible organic extractant, and optionally a non-condensable gas, by distillation and use of an entrainer are provided.

BACKGROUND OF THE INVENTION

Butanol is an important industrial chemical with a variety of applications, such as use as a fuel additive, as a blend component to diesel fuel, as a feedstock chemical in the plastics industry, and as a foodgrade extractant in the food and flavor industry. Each year 10 to 12 billion pounds of butanol are produced by petrochemical means. As the projected demand for butanol increases, interest in producing butanol from renewable resources such as corn, sugar cane, or cellulosic feeds by fermentation is expanding.

In a fermentative process to produce butanol, in situ product removal advantageously reduces butanol inhibition of the microorganism and improves fermentation rates by controlling butanol concentrations in the fermentation broth. Technologies for in situ product removal include stripping, adsorption, pervaporation, membrane solvent extraction, and liquid-liquid extraction. In liquid-liquid extraction, an extractant is contacted with the fermentation broth to partition the butanol between the fermentation broth and the extractant phase. The butanol and the extractant are recovered by a separation process, for example by distillation. In the recovery process, the butanol can also be separated from any water, non-condensable gas, and/or fermentation by-products which may have been removed from the fermentation broth through use of the extractant.

Copending U.S. patent application Ser. No. 12/478,389 filed on Jun. 4, 2009, discloses methods for producing and recovering butanol from a fermentation broth, the methods comprising the step of contacting the fermentation broth with a water immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof, to form a two-phase mixture comprising an aqueous phase and a butanol-containing organic phase.

Copending U.S. Provisional Patent Application Nos. 61/168,640; 61/168,642; and 61/168,645; filed concurrently on Apr. 13, 2009; and 61/231,697; 61/231,698; and 61/231,699; filed concurrently on Aug. 6, 2009, disclose methods for producing and recovering butanol from a fermentation medium, the methods comprising the step of contacting the fermentation medium with a water-immiscible organic extractant comprising a first solvent and a second solvent, the first solvent being selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof, and the second solvent being selected from the group consisting of $C_7$ to $C_{11}$ alcohols, $C_7$ to $C_{11}$ carboxylic acids, esters of $C_7$ to $C_{11}$ carboxylic acids, $C_7$ to $C_{11}$ aldehydes, and mixtures thereof, to form a two-phase mixture comprising an aqueous phase and a butanol-containing organic phase.

Copending U.S. Provisional Patent Application Nos. 61/225,659 and 61/225,662, filed concurrently on Jul. 15, 2009, disclose processes for separating butanol from a mixture comprising butanol, water, a water-immiscible organic extractant, and optionally a non-condensable gas.

Processes for recovering butanol from a butanol-containing extractant phase obtained by in situ product removal from a fermentation broth continue to be sought. Economical processes for recovering butanol substantially free of water and of the extractant are desired. Also desired are separation processes which are energy efficient and provide high purity butanol product having little color. Butanol recovery processes which can be run for extended periods without equipment fouling or repeated shutdowns are also sought.

SUMMARY OF THE INVENTION

The present invention provides a process for separating a butanol selected from the group consisting of 1-butanol, 2-butanol, isobutanol, and mixtures thereof, from a feed comprising a water-immiscible organic extractant, water, the butanol, and optionally a non-condensable gas. The separation is made through a combination of distillation, decantation, and use of an entrainer.

In one aspect, the present invention is a process comprising the steps:

a) introducing a feed comprising:
  (i) a water-immiscible organic extractant,
  (ii) water,
  (iii) at least one isomer of butanol,
  (iv) optionally a non-condensable gas
  into a first distillation column, wherein the first distillation column comprises a stripping section and optionally a rectifying section at an introduction point above the stripping section, the first distillation column having an operating temperature, $T_1$ and an operating pressure $P_1$ at a predetermined point in the stripping section, wherein $T_1$ and $P_1$ are selected to produce a first bottoms stream and a first vaporous overhead stream, the first bottoms stream comprising the water-immiscible organic extractant and butanol and being substantially free of water, and the first vaporous overhead stream comprising water, butanol, optionally the extractant, and optionally the non-condensable gas;

b) introducing a water-immiscible organic entrainer to at least one appropriate process stream or vessel;

c) condensing the first vaporous overhead stream to produce a gas phase and recover a mixed condensate, wherein the mixed condensate comprises:
  (i) an organic phase comprising butanol, entrainer, and water; and
  (ii) an aqueous phase comprising water and butanol; and wherein the mixed condensate comprises sufficient entrainer to provide phase separation of the organic and the aqueous phases;

d) introducing at least a portion of the organic phase to the first distillation column; and e) introducing at least a portion of the first bottoms stream into a second distillation column having at least a stripping section and optionally a rectifying section and operating the second distillation column to produce a second bottoms stream comprising the extractant, and a second vaporous overhead stream comprising butanol;

wherein the extractant is selected such that it (A) preferentially extracts butanol over water and (B) is separable from butanol by distillation; and the entrainer is selected such that it (C) has a higher vapor pressure than butanol and (D) is separable from butanol by distillation.

In embodiments, the entrainer comprises at least one hydrocarbon selected from the group consisting of pentane, hexane, hexene, cyclohexane, benzene, toluene, and xylene. In embodiments, the extractant comprises at least one solvent selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides, and mixtures thereof. In embodiments, the extractant comprises at least one solvent selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. In embodiments, the extractant comprises oleyl alcohol. In embodiments, the butanol comprises 1-butanol, 2-butanol, isobutanol, or a mixture thereof. In embodiments, the feed further comprises ethanol and the second vaporous overhead stream further comprises ethanol. In embodiments, the butanol in the feed introduced into a first distillation column is produced by fermentation of a feedstock such as corn or sugar cane. In embodiments, there is a process to process heat exchange between the feed introduced to the first distillation column and the first bottoms stream.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

The following definitions are used in this disclosure:

Butanol as used herein means 1-butanol (1-BuOH), 2-butanol (2-BuOH), and/or isobutanol (iBuOH or I-BUOH), individually or as mixtures thereof.

"In Situ Product Removal" as used herein means the selective removal of a specific fermentation product from a biological process such as fermentation to control the product concentration in the biological process.

"Fermentation broth" as used herein means the mixture of water, sugars, dissolved solids, suspended solids, microorganisms producing butanol, product butanol and all other constituents of the material held in the fermentation vessel in which product butanol is being made by the reaction of sugars to butanol, water and carbon dioxide ($CO_2$) by the microorganisms present. The fermentation broth is the aqueous phase in biphasic fermentative extraction. From time to time, as used herein the term "fermentation medium" may be used synonymously with "fermentation broth".

"Fermentation vessel" as used herein means the vessel in which the fermentation reaction by which product butanol is made from sugars is carried out. The term "fermentor" may be used synonymously herein with "fermentation vessel".

The term "effective titer" as used herein, refers to the total amount of butanol produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "aqueous phase titer" as used herein, refers to the concentration of butanol in the fermentation broth. Where indicated, the term also refers to the concentration of ethanol in the fermentation broth.

"Stripping" as used herein means the action of transferring all or part of a volatile component from a liquid stream into a gaseous stream.

"Stripping section" as used herein means that part of the contacting device in which the stripping operation takes place.

"Rectifying" as used herein means the action of transferring all or part of a condensable component from a gaseous stream into a liquid stream in order to separate and purify lower boiling point components from higher boiling point components.

"Rectifying section" as used herein means the section of the distillation column above the feed point, i.e. the trays or packing material located above the point in the column where the feed stream enters, where the rectifying operation takes place.

The term "separation" as used herein is synonymous with "recovery" and refers to removing a chemical compound from an initial mixture to obtain the compound in greater purity or at a higher concentration than the purity or concentration of the compound in the initial mixture.

The term "water-immiscible" refers to a chemical component, such as an extractant or solvent, which is incapable of mixing with an aqueous solution, such as a fermentation broth, in such a manner as to form one liquid phase.

The term "extractant" as used herein refers to one or more organic solvents which are used to extract butanol from a fermentation broth.

The term "entrainer" as used herein refers to a third organic component which, when added to an azeotrope formed by a binary mixture, either facilitates or improves the separation of the components of the binary mixture into two liquid phases.

The term "organic phase", as used herein, refers to the non-aqueous phase of a biphasic mixture obtained by contacting a fermentation broth with a water-immiscible organic extractant.

The term "fatty acid" as used herein refers to a carboxylic acid having a long, aliphatic chain of $C_7$ to $C_{22}$ carbon atoms, which is either saturated or unsaturated.

The term "fatty alcohol" as used herein refers to an alcohol having a long, aliphatic chain of $C_7$ to $C_{22}$ carbon atoms, which is either saturated or unsaturated.

The term "fatty aldehyde" as used herein refers to an aldehyde having a long, aliphatic chain of $C_7$ to $C_{22}$ carbon atoms, which is either saturated or unsaturated.

The term "fatty amide" as used herein refers to an amide having a long, aliphatic chain of $C_{12}$ to $C_{22}$ carbon atoms, which is either saturated or unsaturated.

Non-condensable gas means a gas that is not condensed at an operating temperature of the process described herein.

The terms "° C." and "C" mean degrees Celsius.

The term "deg" means degrees.

The term "g/L" means grams per liter.

The term "ppm" means parts per million.

The term "kg/hr" means kilograms per hour.

The term "atm" means atmosphere.

Butanol-containing extractant streams useful as a feed in the processes of the invention include any organic phase obtained from an extractive fermentation wherein butanol is produced as a fermentation product. Typical butanol-containing extractant streams include those produced in "dry grind" or "wet mill" fermentation processes in which in situ product removal is practiced using liquid-liquid extraction of the fermentation broth with an organic extractant. After extraction, the extractant stream typically comprises butanol, water, and the extractant. The extractant stream may optionally comprise a non-condensable gas, which can be a gas that is inert or otherwise non-reactive with other feed components under the operating conditions of the present invention. Such gases can be selected from gases in the group consisting of, for example, carbon dioxide, nitrogen, hydrogen, noble gases such as argon, or mixtures of any of these. The extractant stream may optionally further comprise fermentation by-products having sufficient solubility to partition into the extractant phase. The extractant stream may optionally contain solids, for example biomass or solids from the fermentation. Butanol-containing extractant streams useful as a feed in the processes of the invention include streams characterized by a butanol concentration in the feed from about 0.1 weight percent to about 40 weight percent, for example from about 2 weight percent to about 40 weight percent, for example from about 5 weight percent to about 35 weight percent, based on the weight of the feed. Depending on the efficiency of the extraction, the aqueous phase titer of butanol in the fermentation broth can be, for example, from about 5 g/L to about 85 g/L, or from about 10 g/L to about 40 g/L. In embodiments, the effective titer of butanol recovered from the process is at least about 40 g/L, at least about 50 g/L, at least about 60 g/L, at least about 70 g/L, at least about 80 g/L, at least about 90 g/L or at least about 100 g/L, or any intermediate increment.

Butanol-containing extractant streams useful as a feed may further comprise ethanol. Such extractant streams may be characterized by a butanol concentration as described above herein and by an ethanol concentration in the feed from about 0.01 weight percent to about 10 weight percent, for example from about 0.2 weight percent to about 2 weight percent, for example from about 0.5 weight percent to about 1 weight percent, based on the weight of the feed. Depending on the efficiency of the extraction, the aqueous phase titer of ethanol in the fermentation broth can be, for example, from about 0.1 g/L to about 20 g/L, or from about 1 g/L to about 5 g/L. The ethanol may be obtained in the fermentation broth as a by-product from recombinant butanol-producing microorganisms, for example.

The extractant is a water-immiscible organic solvent or solvent mixture having characteristics which render it useful for the extraction of butanol from a fermentation broth. The extractant preferentially partitions butanol from the aqueous phase, for example by at least a 1.1:1 concentration ratio, such that the concentration of butanol in the extractant phase is at least 1.1 times that in the aqueous phase when evaluated in a room-temperature extraction of an aqueous solution of butanol. In embodiments, the extractant preferentially partitions butanol from the aqueous phase by at least a 2:1 concentration ratio, such that the concentration of butanol in the extractant phase is at least two times that in the aqueous phase when evaluated in a room-temperature extraction of an aqueous solution of butanol. In embodiments, the extractant preferentially partitions butanol from the aqueous phase by at least a 3:1 concentration ratio, by at least a 4:1 concentration ratio, by at least a 5:1 concentration ratio, by at least a 6:1 concentration ratio, by at least a 8:1 concentration ratio, by at least a 10:1 concentration ratio or by at least a 20:1 concentration ratio.

To be of practical use in the butanol recovery process, the extractant is separable from butanol by distillation, having a boiling point at atmospheric pressure which is at least about 30 degrees Celsius higher than that of the butanol to be recovered, or for example at least about 40 degrees higher, or for example at least about 50 degrees higher. A mixture of higher boiling extractants is expected to behave in a fundamentally similar way to a single extractant provided that the boiling point of the mixture, or the boiling point of the lowest boiling solvent of the mixture, is significantly higher than the boiling points of water and butanol, for example at least about 30 degrees higher.

The extractant can comprise at least one solvent selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides, and mixtures thereof. The extractant can comprise at least one solvent selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. Examples of suitable extractants include an extractant comprising at least one solvent selected from the group consisting of oleyl alcohol, behenyl alcohol, cetyl alcohol, lauryl alcohol, myristyl alcohol, stearyl alcohol, oleic acid, lauric acid, myristic acid, stearic acid, methyl myristate, methyl oleate, lauric aldehyde, 1-nonanol, 1-decanol, 1-undecanol, 2-undecanol, 1-nonanal, 2-butyloctanol, 2-butyl-octanoic acid and mixtures thereof. In embodiments, the extractant comprises oleyl alcohol. In embodiments, the extractant comprises a branched chain saturated alcohol, for example, 2-butyloctanol, commercially available as ISOFAL® 12 (Sasol, Houston, Tex.) or Jarcol I-12 (Jarchem Industries, Inc., Newark, N.J.). In embodiments, the extractant comprises a branched chain carboxylic acid, for example, 2-butyl-octanoic acid, 2-hexyl-decanoic acid, or 2-decyl-tetradecanoic acid, commercially available as ISOCARB® 12, ISOCARB® 16, and ISOCARB® 24, respectively (Sasol, Houston, Tex.).

Such organic extractants can be available commercially from various sources, such as Sigma-Aldrich (St. Louis, Mo.), in various grades, many of which may be suitable for use in extractive fermentation to produce or recover butanol. Technical grades contain a mixture of compounds, including the desired component and higher and lower fatty components. For example, one commercially available technical grade oleyl alcohol contains about 65% oleyl alcohol and a mixture of higher and lower fatty alcohols.

The invention provides processes for separating or recovering butanol from a feed comprising a water-immiscible organic extractant, water, at least one isomer of butanol, and optionally a non-condensable gas. Separation of the butanol from the feed is achieved through a combination of distillation, decantation, and the use of an entrainer. The distillation involves the use of at least two distillation columns. The first column, in combination with the entrainer and decantation, effects a separation of water from butanol and the extractant, for example oleyl alcohol. The entrainer is added to an appropriate process stream or vessel in an amount such that the mixed condensate from the first column contains sufficient entrainer to provide phase separation of the organic and the aqueous phases. Such phase separation typically occurs in a decanter. By "phase separation" is meant the physical formation of two liquid phases, one mostly aqueous and one mostly organic, from one initial liquid phase containing water and organics. The physical characteristics of the entrainer and its concentration in the initial liquid phase, as well as the concentrations of butanol and ethanol in the initial liquid phase, determine if phase separation occurs under the selected process conditions. Temperature and pressure, for example, can also affect phase separation. The organic phase is returned to the first column. The second column effects a separation of butanol from the extractant under vacuum conditions and provides a butanol stream which is substantially free of extractant and substantially free of entrainer. The second column also provides an extractant stream which is substantially free of water and has a reduced butanol content. By "substantially free of extractant" it is meant that less than about 0.01 weight percent of extractant is present in the stream. By "substantially free of entrainer" it is meant that less than about 0.01 weight percent of entrainer is present in the stream.

The entrainer is a water-immiscible organic compound having characteristics which render it useful in the processes of the invention. The entrainer has a sufficiently higher vapor pressure and is more volatile than the butanol isomer to be separated (or than the most volatile butanol isomer in a mixture of butanol isomers) to enable its use in the distillations described herein. For example, when the operating conditions of the first and/or second distillation columns include using about atmospheric pressure at the tops of the columns, the difference in vapor pressure between the entrainer and the most volatile butanol isomer may be about 5 to about 50 psi. When the operating conditions include using less than atmospheric pressure at the tops of the distillation columns, the difference in vapor pressure may be smaller, for example about 10 to about 30 psi. Using an entrainer which is too volatile in relation to the butanol can result in excessive entrainer losses during separation or require much colder chilling media to condense and recover the entrainer. To be suitable for use, the entrainer also has a low molar latent heat, is thermally stable under the operating conditions of the process, and is inert or otherwise non-reactive with other components in the feed stream.

To be of practical use in the butanol recovery process, the entrainer is separable from butanol by distillation and has a boiling point at atmospheric pressure which is lower than that of the butanol to be recovered.

The entrainer can comprise at least one hydrocarbon. The entrainer can be, for example, a saturated or unsaturated, substituted or unsubstituted, aliphatic hydrocarbon. The entrainer can be a substituted or unsubstituted aromatic hydrocarbon. For example, the entrainer may comprise at least one hydrocarbon selected from the group consisting of pentane, hexane, hexene, cyclohexane, benzene, toluene, and xylene. Preferably, the entrainer comprises hexane.

Figure 1:
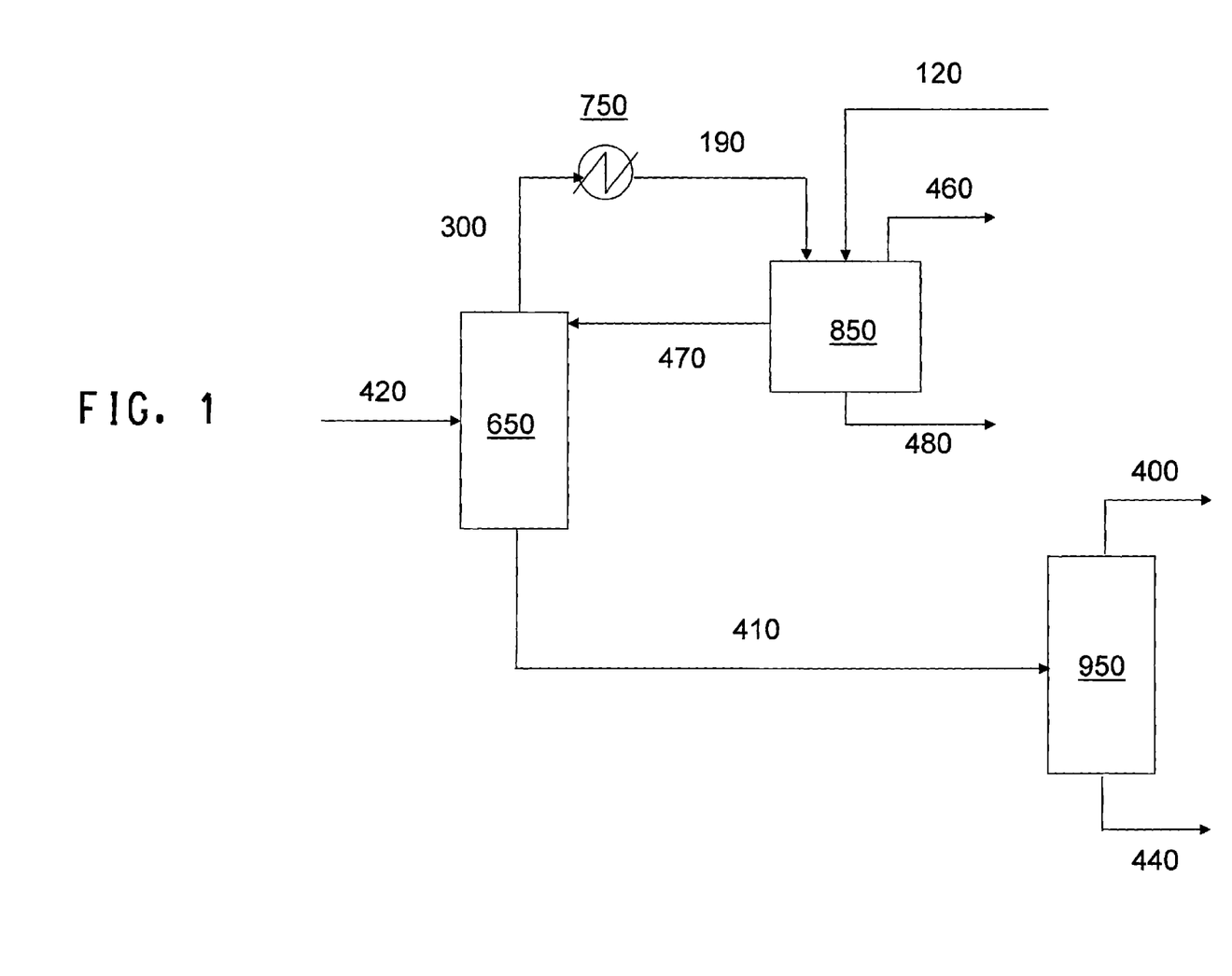
FIG. 1 illustrates one embodiment of a system useful for practicing the process of the invention.

The processes of the invention can be understood by reference to FIG. 1, which illustrates one embodiment of a system useful for practicing the process of the invention. The feed stream 420, obtained from a fermentation vessel (not shown) or an extractor (not shown) in a process for fermentative extraction, is introduced into a first distillation column 650, which has a stripping section and optionally a rectifying section, at a feed point above the stripping section. The feed stream 420 is distilled to provide a first bottoms stream 410 and a first vaporous overhead stream 300 comprising water, butanol, entrainer, and any non-condensable gas present in the feed. An operating temperature $T_1$ and an operating pressure $P_1$ at a predetermined point in the stripping section of column 650 are selected so as to provide the first bottoms stream 410 comprising the extractant and butanol and being substantially free of water and substantially free of entrainer. The distillation column 650 can be any conventional column having at least a feed inlet, an overhead vapor outlet, a bottoms stream outlet, a heating means, and a sufficient number of stages to effect the separation of the water from the extractant. In the case where the extractant comprises oleyl alcohol, distillation column 650 should have at least 5 stages including a re-boiler.

The first bottoms stream 410 can comprise from about 0.1 to about 40 weight percent butanol, and can be substantially free of water. By "substantially free of water", it is meant that the bottoms stream can comprise less than about 0.01 weight percent water. By "substantially free of entrainer" it is meant that the entrainer comprises no more than about 0.01 weight percent of the bottoms 410. To ensure that the bottom stream 410 is substantially free of water, the amount of organic phase reflux and the reboiler boil-up rate can be varied.

The vaporous overhead stream 300 from the first distillation column can include up to about 66 weight percent butanol and from about 23 to about 40 weight percent water. Overhead stream 300 can also include about 30 to about 70 weight percent entrainer. When more entrainer is used in the process than the minimal amount sufficient to provide phase separation of the mixed condensate under the selected operating conditions, the amount of entrainer in stream 300 is proportionately increased, and the weight percentages of butanol and water are proportionately decreased. The overhead stream includes non-condensable gas that may have been present in the feed. Stream 300 is condensed in a condenser 750 to produce a mixed condensate stream 190 comprising condensed liquid organics and condensed liquid water. The mixed condensate stream 190 should comprise sufficient entrainer to provide phase separation of the organic and the aqueous phases. Stream 190 also includes any non-condensable gas present in the feed. The condenser 750 may be of any conventional design.

The mixed condensate stream 190 is introduced into a decanter 850 and allowed to separate into a liquid organic phase and a liquid aqueous phase. The temperature of the decanter is preferably maintained at or below about 40° C. to reduce the amount of butanol, entrainer, and water being stripped out by the non-condensable gas. The liquid organic phase, the top liquid phase, can include less than about 5 weight percent water, or less than about 2 weight percent water and may further comprise any extractant which comes overhead in column 650. When more entrainer is used in the process than the minimal amount sufficient to provide phase separation of the mixed condensate under the selected operating conditions, the amount of entrainer in the liquid organic phase is proportionately increased, and the weight percentages of butanol and water are proportionately decreased. The fraction of extractant in the organic phase can be minimized by use of an optional rectification section in column 650. The liquid aqueous phase includes less than about 25 weight percent, or from about 10 to about 20 weight percent, butanol. The liquid aqueous phase can include less than about 5 weight percent entrainer, or less than about 1 weight percent entrainer. The decanter may be of any conventional design.

When a non-condensable gas such as carbon dioxide is present in the feed, the non-condensable gas is present in stream 300 and in stream 190. The process may further comprise the step of purging at least a portion of the gas phase comprising the non-condensable gas from the process, as shown in FIG. 1, in which purge stream 460 comprising the non-condensable gas is shown leaving the decanter 850. Purge stream 460 can further comprise entrainer. To minimize the amount of entrainer which is lost through this purge stream, stream 460 can be partially condensed to recover a portion of the entrainer contained therein, and the recovered entrainer can be returned to the process (not shown). In one embodiment, the process can further comprise the step of partially condensing the gas phase to recover at least a portion of the entrainer and optionally introducing the recovered entrainer to the mixed condensate.

From the decanter 850, the aqueous phase 480 can be purged from the process, as shown in FIG. 1, in which the purge stream comprising the aqueous phase 480 is shown leaving the decanter 850. Alternatively, at least a portion of the aqueous phase can be introduced to a fermentation vessel (not shown). This can provide a means to recycle some of the water from the butanol recovery process back to the extractive fermentation process. In one embodiment, at least a portion of the aqueous phase 480 can be combined with at least a portion of the bottoms stream 440 from the second distillation column and then introduced to a fermentation vessel (not shown).

The organic phase 470 from the decanter is returned to the first distillation column 650. Stream 470 would normally be introduced as reflux to the column. Introducing stream 470 as liquid reflux will suppress extractant loss in vaporous stream 300 of column 650. The organic phase 470 may further comprise volatile fermentation byproducts such as acetaldehyde. Optionally, at least a portion of stream 470 may be purged from the process (not shown) to remove volatile fermentation byproducts from the butanol recovery process. Such a purge stream can represent a potential loss of entrainer, which can be compensated for by the introduction of additional entrainer to the process.

The first bottoms stream 410 is withdrawn from column 650 and introduced into a second distillation column 950, which has a stripping section and optionally a rectifying section, at a feed point above the stripping section. The stream 410 is distilled to provide a second bottoms stream 440 comprising the extractant and a second vaporous overhead stream 400 comprising butanol. The second distillation column is operated so as to provide the bottoms stream 440 substantially free of butanol and substantially free of entrainer. By "substantially free of butanol" it is meant that the bottom 440 comprises less than about one weight percent butanol. By "substantially free of entrainer" it is meant that the bottom 440 comprises less than about 0.01 weight percent entrainer. The second vaporous overhead stream 400 is substantially free of the extractant. By "substantially free of extractant" it is meant that the overhead stream 400 comprises less than about 0.01 weight percent extractant. The distillation column 950 can be any conventional column having at least a feed inlet, an overhead vapor outlet, a bottoms stream outlet, a heating means, a stripping section, and a sufficient number of stages to effect the desired separation. Column 950 should have at least 6 stages a including re-boiler. Preferably, column 950 is operated at a pressure less than atmospheric to minimize the temperature of the extractant in the base of the column while enabling economical and convenient condensation of the butanol overheads.

In one embodiment, wherein the second vaporous overhead stream 400 further comprises entrainer, the process further comprises the steps of introducing the second vaporous overhead stream into a third distillation column having at least a stripping section, operating the third distillation column to produce a third bottoms stream comprising butanol and a third vaporous overhead stream comprising the entrainer; and optionally, introducing the third vaporous overhead stream to the mixed condensate (not shown).

The process may further comprise introducing bottoms stream 440 from the second distillation column into a fermentation vessel (not shown). In one embodiment, bottoms stream 440 may be combined with at least a portion of the aqueous phase 480 from the decanter before introduction into a fermentation vessel (not shown).

In one embodiment, feed stream 420 further comprises ethanol. As described herein above, the feed stream 420 is distilled in the first distillation column 650 to provide the first bottoms stream 410, which comprises the extractant, butanol, and ethanol and is substantially free of water and substantially free of entrainer, and the first vaporous overhead stream 300, which comprises water, butanol, entrainer, ethanol, and any non-condensable gas present in the feed. The first bottoms stream 410 can include less than about 50 weight percent butanol, less than about 10 weight percent ethanol, and less than about 0.01 weight percent entrainer. Feed stream 420 comprising butanol and ethanol is introduced into column 650 at a feed point above the stripping section.

When the feed comprises butanol and ethanol, the vaporous overhead stream 300 from the first distillation column can include 10 to about 40 weight percent butanol, about 1 to about 10 weight percent ethanol, about 10 to about 50 weight percent water, and about 30 to about 60 weight percent entrainer. The composition of stream 300 will depend on the composition of the feed stream, the operating conditions of the first column (for example temperature and pressure), and the amount of entrainer circulating in the process. When more entrainer is used in the process than about the minimal amount sufficient to provide phase separation of the mixed condensate under the selected operating conditions, the amount of entrainer in stream 300 is proportionately increased, and the weight percentages of butanol, ethanol, and water are proportionately decreased. Condensation of stream 300 produces the mixed condensate stream 190, which should comprise sufficient entrainer to provide phase separation of the organic and the aqueous phases. The liquid organic phase comprises butanol, entrainer, ethanol, and optionally the extractant. The liquid organic phase can contain less than about 80 weight percent entrainer, or from about 40 to about 70 weight percent entrainer. The liquid aqueous phase is substantially free of entrainer and comprises water, butanol, and ethanol. The liquid aqueous phase can contain less than about 0.1 weight percent entrainer.

As disclosed above herein, the first bottoms stream 410 is introduced to the second distillation column 950 and distilled to provide a second bottoms stream 440 and a second vaporous overhead stream 400. When the feed stream 420 comprises butanol and ethanol, the second vaporous overhead stream 400 also comprises butanol and ethanol. In general, operating conditions for the first and second columns can be selected to maintain about the same ratio (on a mass basis) of ethanol to butanol in stream 400 as in feed stream 420. The second bottoms stream 440 comprises extractant and is substantially free of butanol and ethanol. The vaporous overhead stream 400 can contain from about 70 weight percent to about 99 weight percent butanol, from about 1 weight percent to about 30 weight percent ethanol, and optionally less than about 0.1 weight percent entrainer.

As shown in FIG. 1, entrainer can be added as stream 120 to the decanter 850. Other alternative methods (not shown) of introducing the entrainer to at least one appropriate process stream or vessel include adding the entrainer (or a stream comprising the entrainer) to the feed stream 420, the first vaporous overhead stream 300, the mixed condensate stream 190, the first distillation column 650, or combinations thereof.

The entrainer can be introduced to any appropriate point or points in the portion of the process through which the entrainer circulates. Appropriate process streams or vessels to which the entrainer (or a stream comprising the entrainer) can be added include the feed stream 420, the first vaporous overhead stream 300, the mixed condensate stream 190, the first distillation column 650, the decanter 850, and combinations thereof. Shown in FIG. 1 is addition of the entrainer as stream 120 to the decanter 850. When the stream to which the entrainer is introduced is vaporous, the entrainer is preferably preheated and added as a vaporous stream.

Addition of the entrainer to the process can be performed in a continuous manner or in a discontinuous manner, so long as the amount of entrainer in the mixed condensate is sufficient to provide phase separation of the organic and the aqueous phases under the operating conditions of the process. An amount of entrainer in excess of that required for phase separation can be used but as this can lead to increased volumes of the process streams comprising the entrainer, increased energy consumption, proportionally larger loss of entrainer from the process, and increased operating cost, the use of significantly excess entrainer in the process is typically not desirable. Use of about the minimal amount of entrainer which is sufficient to provide phase separation under the selected operating conditions can be preferred. Typically, make-up entrainer is added to the process to compensate for the entrainer losses which can be incurred when vaporous streams exit the process.

The present processes for separating or recovering butanol provide butanol known to have an energy content similar to that of gasoline and which can be blended with any fossil fuel. Butanol is favored as a fuel or fuel additive as it yields only $CO_2$ and little or no $SO_X$ or $NO_X$ when burned in the standard internal combustion engine. Additionally, butanol is less corrosive than ethanol, the most preferred fuel additive to date.

In addition to its utility as a biofuel or fuel additive, the butanol recovered according to the present processes has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles. Furthermore, the present processes recover butanol obtained from plant derived carbon sources, avoiding the negative environmental impact associated with standard petrochemical processes for butanol production.

One advantage of the present processes for separation or recovery of butanol is energy integration of the distillation columns, which provides energy efficiency. Relative to a distillation scheme in which the separation of butanol and extractant is made prior to the final separation of butanol and water, the present processes require less energy per unit weight of butanol obtained.

Another advantage is that the present processes provide high purity butanol having little or no color.

A further advantage is that the second bottoms stream comprising the extractant is substantially free of the butanol product, which contributes to high yield in the recovery process. Being substantially free of butanol also enables optional recycling of the second bottoms stream comprising the extractant to the fermentative process. Being substantially free of butanol also simplifies the stream's disposition, should it not be recycled.

Yet another advantage is that the present processes allow for extended operation without equipment fouling or repeated shutdowns.

Although particular embodiments of the present invention have been described in the foregoing description, it will be understood by those skilled in the art that the invention is capable of numerous modifications, substitutions, and rearrangements without departing from the spirit of essential attributes of the invention. Reference should be made to the appended claims, rather than to the foregoing specification, as indicating the scope of the invention.

The process of the invention can be demonstrated using a computational model of the process. Process modeling is an established methodology used by engineers to simulate complex chemical processes. Process modeling software performs many fundamental engineering calculations, for example mass and energy balances, vapor/liquid equilibrium and reaction rate computations. The modeling of distillation columns is particularity well established. Calculations based on experimentally determined binary vapor/liquid equilibrium and liquid/liquid equilibrium data can predict reliably the behavior of multi-component mixtures. This capability has been expanded to allow modeling of complex multi-stage, multi-component distillation columns using rigorous algorithms like the "inside-out" algorithm developed by Joseph Boston of Aspentech, Inc. of Burlington, Mass. Commercial modeling software, such as Aspen Plus® from Aspentech, can be used in conjunction with physical property databases, such as DIPPR, available from the American Institute of Chemical Engineers, Inc., of New York, N.Y., to develop accurate models and assessments of processes.

EXAMPLES

Examples 1 and 2 were obtained through process modeling using 2-butanol as the butanol isomer, oleyl alcohol as the extractant, and n-hexane as the entrainer. Examples 3 and 4 were obtained through process modeling using isobutanol as the butanol isomer, oleyl alcohol as the extractant, and n-hexane as the entrainer. A small amount of ethanol was included in the feed stream for Examples 3 and 4.

Similar results would be expected for the analogous cases where 1-butanol or mixtures of 1-butanol, 2-butanol, and/or isobutanol were selected as the butanol isomer.

Table 1 lists typical feed compositions of the rich solvent stream, obtained from extractive fermentation, entering the alcohol product recovery area. These compositions were used in modeling the processes of the invention. In the Examples, the term "rich solvent stream" is synonymous with the term "feed stream" used above.

TABLE 1

Feed Compositions (in Weight Percent) of the Rich Solvent Stream from the Extractor

| Feed Compositions | Example 1 | Example 2 | Example 3 | Example 4 |
|---|---|---|---|---|
| Iso-butanol | — | — | 5.4% | 5.375% |
| 2-butanol | 5.40% | 13.84% | — | — |
| Ethanol | — | — | 0.54% | 0.9954% |
| Water | 7.20% | 9.58% | 7.2% | 7.167% |
| Carbon dioxide | 0.20% | 0.75% | 0.2% | 0.199% |
| Oleyl alcohol | 87.2% | 75.83% | 86.66% | 86.26% |

These composition values for the rich solvent stream were established by a simulation of a dry grind facility using extractive in situ product removal technology producing 50 mM gal/year of 2-butanol or isobutanol, and fermenter broth aqueous phase titers of 10 and 40 g/L 2-butanol or 10 g/L isobutanol respectively. It was assumed that the rich solvent stream was at equilibrium with the fermentation broth and that the solvent flow rate was sufficient to meet the specified annual capacity.

Figure 2:
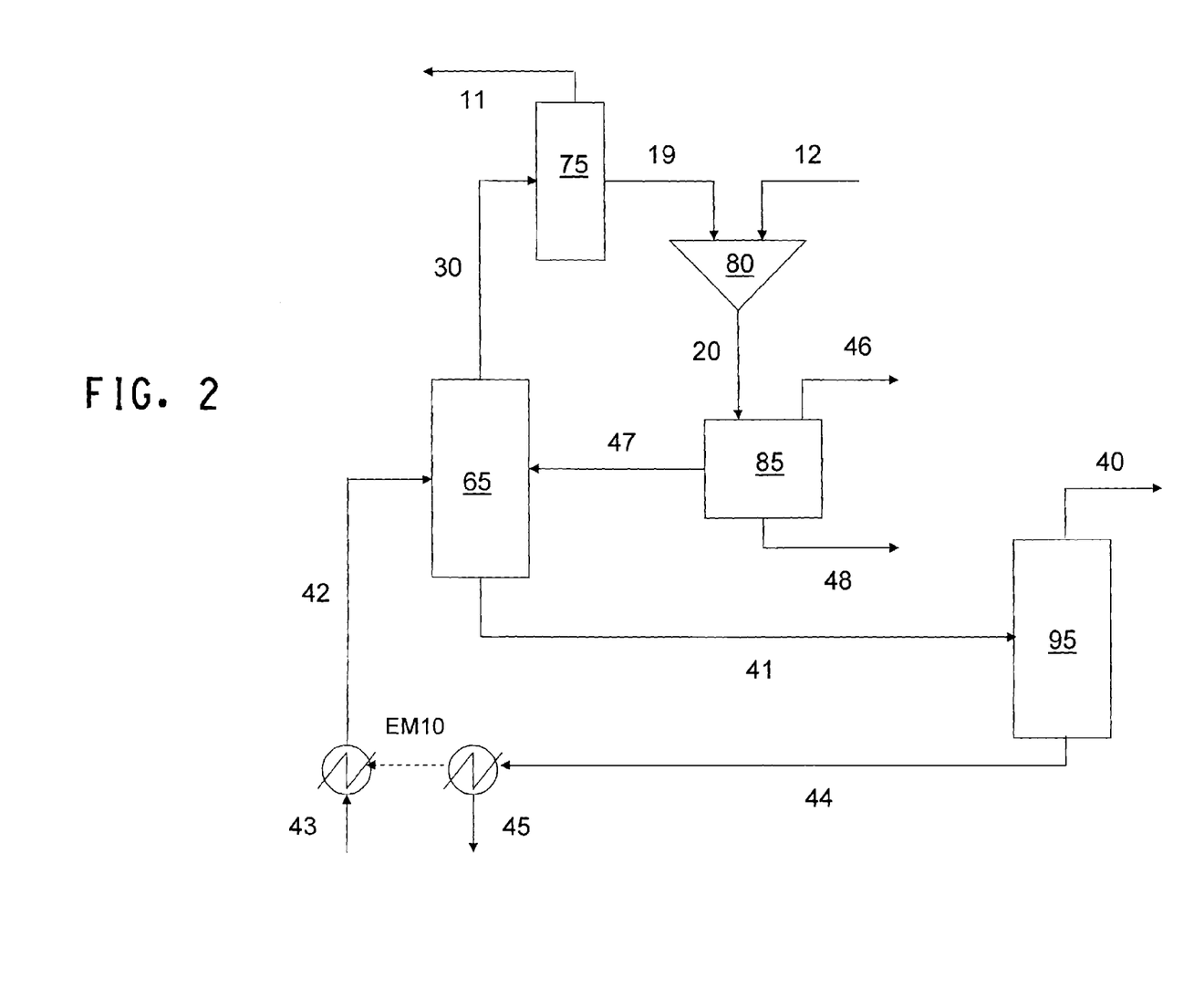
FIG. 2 illustrates a process schematic diagram used in modeling example embodiments of the process of the invention.

The parameters inputted for the simulations of the embodiments of the processes of the invention are listed in Table 2 and follow a process schematic diagram as shown in FIG. 2. In FIG. 2, "EM10" refers to a heat stream representing process to process heat exchange between the solvent column feed and bottom product via heat exchangers. Block 80 represents a mixer combining the two streams 12 and 19. Block 75 represents a modeling artifact where all entrainer is taken out of the process so that the correct amount of entrainer can be added to the decanter. Certain dimensions and duty results calculated from the process model are also listed in Table 2. These parameters do not include physical property parameters, and those related to convergence and other computational options or diagnostics.

lar modification was made to the rich solvent feed flow and compositions from the extractive fermentation process where specific aqueous phase titers were maintained. In each of the independent simulations, column traffic and heat exchanger duties will change because of the feed composition change. By comparing the resulting capital investment and operating costs between different cases, the impact of the rich solvent feed flow and composition on product recovery area performance was quantified. These four examples, however, should not be regarded as process operating limits of this invention.

The term "Solvent Column" is synonymous with the term "first distillation column" used above. The term "BUOH column" is synonymous with the term "second distillation column" used above. The abbreviation "OLEYLOH" refers to oleyl alcohol. The abbreviation "N—C6" refers to n-hexane.

Stream results for Example 1 are listed in Table 3. BUOH column traffic and liquid mass composition profiles are listed in Table 4. Solvent column traffic and liquid mass composition profiles are listed in Table 5.

Stream results for Example 2 are listed in Table 6. BUOH column traffic and liquid mass composition profiles are listed in Table 7. Solvent column traffic and liquid mass composition profiles are listed in Table 8.

TABLE 2

Conditions Used for Modeling Processes of the Invention

| Blocks | Inputs | Example 1 | Example 2 | Example 3 | Example 4 | Units |
|---|---|---|---|---|---|---|
| Solvent Column (65) | Number of theoretical stages including re-boiler | 15 | 15 | 15 | 15 | stages |
| | Column top pressure | 1 | 1 | 1 | 1 | bar |
| | Column bottom pressure | 1.1 | 1.1 | 1.1 | 1.1 | bar |
| | Column internal diameter | 4.43 | 4.09 | 4.44 | 4.39 | m |
| | Column re-boiler duty | 100685 | 71302 | 99716 | 101471 | MJ/hr |
| | Preheated rich solvent feed (42) location | 1 | 1 | 1 | 1 | stage |
| | Organic reflux from decanter (47) location | 1 | 1 | 1 | 1 | stage |
| | Mass fraction water in bottom stream (41) | 1 | 1 | 1 | 1 | ppm |
| | Reflux stream temperature | 35 | 35 | 35 | 35 | deg C. |
| | Preheated rich solvent stream (42) flow rate | 330000 | 131500 | 330000 | 330000 | kg/hr |
| | Preheated rich solvent stream (42) temperature | 98.4 | 86.3 | 98.7 | 98.3 | deg C. |
| | Condenser duty of the solvent column | −40558 | −12360 | −36779 | −38811 | MJ/hr |
| BuOH Column (95) | Number of theoretical stages including re-boiler | 15 | 15 | 15 | 15 | stages |
| | Column top pressure | 0.1 | 0.1 | 0.1 | 0.1 | bar |
| | Column bottom pressure | 0.105 | 0.105 | 0.105 | 0.105 | bar |
| | Column internal diameter | 2.73 | 2.52 | 2.81 | 2.76 | m |
| | Column re-boiler duty | 5202 | 6577 | 7494 | 6061 | MJ/hr |
| | Organic feed from solvent column (41) location | 7 | 7 | 7 | 7 | stage |
| | Organic feed from solvent column (41) temperature | 180.5 | 133.8 | 179 | 180 | deg C. |
| | Solvent mass fraction in overhead product (40) | 100 | 100 | 100 | 100 | ppm |
| | BuOH mass fraction in lean solvent stream (44) | 0.0038 | 0.01 | 0.0044 | 0.0044 | |
| | Lean solvent stream (44) temperature | 180.6 | 134.9 | 180 | 179 | deg C. |
| Decanter (85) | Decanter pressure | 1 | 1 | 1 | 1 | atm |
| | Decanter temperature | 35 | 35 | 35 | 35 | deg C. |
| | Entrainer circulation rate | 28000 | 28000 | 28000 | 28000 | kg/hr |

Four cases were run to demonstrate the operating requirements of the processes of the invention. Examples 1 and 2 were run to demonstrate the separation of 2-butanol from the rich solvent stream. Examples 3 and 4 were run to demonstrate the separation of isobutanol and a small amount of ethanol from the rich solvent stream. For each case, a particu- Stream results for Example 3 are listed in Table 9. BUOH column traffic and liquid mass composition profiles are listed in Table 10. Solvent column traffic and liquid mass composition profiles are listed in Table 11.

Stream results for Example 4 are listed in Table 12. BUOH column traffic and liquid mass composition profiles are listed in Table 13. Solvent column traffic and liquid mass composition profiles are listed in Table 14.

Other key process parameters include the following: 1) the total number of theoretical stages and bottom stream water content in the solvent column; 2) BUOH column bottom temperature and butanol composition in lean solvent stream; 3) the degree of preheating of the rich solvent stream before feeding it to the solvent column; and 4) the amount of entrainer, water, and solvent allowed in the final product. These parameters can be manipulated to achieve optimum separation performance.

Example 1

In this Example, 330,000 kg/hr rich solvent feed 43 containing 5.40 weight percent 2-butanol is heated from 32 to 98.4° C. by a process to process heat exchanger and the resulting stream 42 is fed to the solvent column at stage 1. This rich solvent feed condition corresponds to 10 g/L aqueous phase titer in the fermenter which is maintained during the extractive fermentation process. The separation is realized by a larger diameter solvent column, and higher solvent column re-boiler and condenser duties compared to those of Example 2. The BuOH column bottom temperature is maintained at 180.5° C. which is similar to that of the solvent column bottom stream 41. The resulting residual 2-BuOH composition in the recycle lean solvent stream 44 is 0.38 weight percent. Stream 40 is essentially pure 2-butanol.

Example 2

In this Example, 131,500 kg/hr rich solvent feed 43 containing 13.84 weight percent 2-butanol is heated from 32 to 86.3° C. by a process to process heat exchanger and the resulting stream 42 is fed to the solvent column at stage 1. This rich solvent feed condition corresponds to 40 g/L aqueous phase titer in the fermenter which is maintained during the extractive fermentation process. The separation is realized by a smaller diameter solvent column, and lower solvent column re-boiler and condenser duties due to the lower solvent circulation rate. The BuOH column bottom temperature is maintained at 134.9° C. which is similar to that of the solvent column bottom stream 41. The resulting residual 2-BuOH composition in the recycle lean solvent stream 44 is 1 weight percent. Stream 40 is essentially pure 2-butanol.

Example 3

In this Example, 330,000 kg/hr rich solvent feed 43 containing 5.40 weight percent isobutanol and 0.54 weight percent ethanol is heated from 32 to 98.7° C. by a process to process heat exchanger and the resulting stream 42 is fed to the solvent column at stage 1. This rich solvent feed condition corresponds to 10 g/L aqueous phase isobutanol titer in the fermenter which is maintained during the extractive fermentation process. In addition, a small amount of ethanol is assumed to be present in the fermentation broth. The mass ratio of ethanol to isobutanol in the rich solvent stream is assumed to be 10 wt % in this Example. The BuOH column bottom temperature is maintained at 180° C. which is similar to that of the solvent column bottom stream 41. The resulting residual isobutanol composition in the recycle lean solvent stream 44 is 0.44 weight percent. Stream 40 is 99.1 weight percent isobutanol and 0.9 weight percent ethanol. The separation is realized by a similar diameter solvent column, and a similar solvent column re-boiler and condenser duties as those of Example 1.

Example 4

In this Example, 330,000 kg/hr rich solvent feed 43 is heated from 32 to 98.3° C. by a process to process heat exchanger and the resulting stream 42 is fed to the solvent column at stage 1. This rich solvent feed condition corresponds to 10 g/L aqueous phase isobutanol titer in the fermenter which is maintained during the extractive fermentation process. The mass ratio of ethanol to isobutanol in rich solvent stream is assumed to be 18.5 wt % in this Example. BuOH column bottom temperature is maintained at 179° C. which is similar to that of the solvent column bottom stream 41. The resulting residual isobutanol composition in the recycle lean solvent stream 44 is 0.44 wt %. Stream 40 is 98.3 weight percent isobutanol and 1.7 weight percent ethanol. The separation is realized by a similar diameter solvent column, and a similar solvent column re-boiler and condenser duties as those of Example 1.

TABLE 3

Simulated Stream Outputs for Example 1.

| | 11 | 12 | 19 | 20 | 30 | 40 | 41 | 42 |
|---|---|---|---|---|---|---|---|---|
| Temperature C. | 89.9 | 25 | 89.9 | 74.6 | 89.9 | 48.6 | 180.5 | 98.4 |
| Pressure atm | 0.99 | 2 | 0.99 | 0.99 | 0.99 | 0.1 | 1.09 | 1.05 |
| Vapor Frac | 1 | 0 | 0.511 | 0.458 | 1 | 0 | 0 | 0.366 |
| Mole Flow kmol/hr | 318.845 | 324.932 | 1590.125 | 1915.068 | 1908.969 | 164.584 | 1251.249 | 2646.105 |
| Mass Flow kg/hr | 27475.496 | 28000 | 42601.467 | 70601.841 | 70076.963 | 12198.965 | 301055.406 | 330000 |
| Volume Flow l/hr | 9.29E+06 | 42683.8 | 2.42E+07 | 2.48E+07 | 5.68E+07 | 1.56E+04 | 4.16E+05 | 2.82E+07 |
| Enthalpy MMBtu/hr | −4.75E+01 | −61.151 | −4.05E+02 | −4.66E+02 | −4.22E+02 | −5.26E+01 | −5.06E+02 | −901.367 |
| Mass Flow kg/hr | | | | | | | | |
| 2-BUOH | | | 17692.715 | 17692.938 | 17692.715 | 12197.353 | 13295.008 | 17820 |
| OLEYLOH | | | 15.059 | 15.06 | 15.059 | 1.22 | 287759.999 | 287760 |
| WATER | | | 23966.725 | 23966.884 | 23966.725 | 0.299 | 0.301 | 23760 |
| N—C6 | 27475.496 | 28000 | | 28000 | 27475.496 | 0.093 | 0.099 | |
| CO2 | | | 926.967 | 926.96 | 926.967 | | trace | 660 |

TABLE 3-continued

Simulated Stream Outputs for Example 1.

Mass Frac

| | | | | | | | |
|---|---|---|---|---|---|---|---|
| 2-BUOH | | | 0.415 | 0.251 | 0.252 | 1 | 0.044 | 0.054 |
| OLEYLOH | | | 353 PPM | 213 PPM | 215 PPM | 100 PPM | 0.956 | 0.872 |
| WATER | | | 0.563 | 0.339 | 0.342 | 25 PPM | 1 PPM | 0.072 |
| N—C6 | 1 | 1 | | 0.397 | 0.392 | 8 PPM | 328 PPB | |
| CO2 | | | 0.022 | 0.013 | 0.013 | | trace | 0.002 |

| | | 43 | 44 | 45 | 46 | 47 | 48 |
|---|---|---|---|---|---|---|---|
| | Temperature C. | 32.2 | 180.6 | 45 | 35 | 35 | 35 |
| | Pressure atm | 1.05 | 0.11 | 1.26 | 1 | 1 | 1 |
| | Vapor Frac | 0 | 0 | 0 | 1 | 0 | 0 |
| | Mole Flow kmol/hr | 2646.105 | 1086.664 | 1086.664 | 21.997 | 514.114 | 1378.958 |
| | Mass Flow kg/hr | 330000 | 288856.441 | 288856.441 | 1210.227 | 41132.392 | 28259.222 |
| | Volume Flow l/hr | 390735.36 | 396285.432 | 348575.397 | 547908.29 | 59774.124 | 29475.208 |
| | Enthalpy MMBtu/hr | −986.805 | −459.209 | −544.647 | −6.66 | −122.164 | −375.55 |
| | Mass Flow kg/hr | | | | | | |
| | 2-BUOH | 17820 | 1097.654 | 1097.654 | 44.082 | 13167.746 | 4481.11 |
| | OLEYLOH | 287760 | 287758.779 | 287758.779 | trace | 15.058 | 0.001 |
| | WATER | 23760 | 0.002 | 0.002 | 21.752 | 207.026 | 23738.106 |
| | N—C6 | | 0.006 | 0.006 | 522.477 | 27475.595 | 1.928 |
| | CO2 | 660 | | | 621.916 | 266.967 | 38.077 |
| | Mass Frac | | | | | | |
| | 2-BUOH | 0.054 | 0.004 | 0.004 | 0.036 | 0.32 | 0.159 |
| | OLEYLOH | 0.872 | 0.996 | 0.996 | trace | 366 PPM | 39 PPB |
| | WATER | 0.072 | 6 PPB | 6 PPB | 0.018 | 0.005 | 0.84 |
| | N—C6 | | 21 PPB | 21 PPB | 0.432 | 0.668 | 68 PPM |
| | CO2 | 0.002 | | | 0.514 | 0.006 | 0.001 |

TABLE 4

Simulated BUOH Column Traffic and Liquid Mass Composition Profile Outputs for Example 1.

| Stage | Temperature C. | Pressure atm | Heat duty MJ/hr | Liquid flow kg/hr | Vapor flow kg/hr | Liquid feed kg/hr |
|---|---|---|---|---|---|---|
| 1 | 48.647935 | 0.1 | −11327.359 | 4896.92422 | 0 | 0 |
| 2 | 63.685956 | 0.100357 | 0 | 1766.54168 | 17095.8892 | 0 |
| 3 | 162.40147 | 0.100714 | 0 | 2385.02432 | 13965.5067 | 0 |
| 4 | 172.35129 | 0.101071 | 0 | 2488.46436 | 14583.9893 | 0 |
| 5 | 173.31688 | 0.101429 | 0 | 2495.24895 | 14687.4294 | 0 |
| 6 | 173.4506 | 0.101786 | 0 | 2492.49603 | 14694.2139 | 0 |
| 7 | 173.50353 | 0.102143 | 0 | 288999.473 | 143.073499 | 286507.018 |
| 8 | 173.50628 | 0.1025 | 0 | 289004.764 | 143.032473 | 0 |
| 9 | 173.50903 | 0.102857 | 0 | 289010.05 | 148.322751 | 0 |
| 10 | 173.51178 | 0.103214 | 0 | 289015.334 | 153.609067 | 0 |
| 11 | 173.51453 | 0.103571 | 0 | 289020.616 | 158.892612 | 0 |
| 12 | 173.51728 | 0.103929 | 0 | 289025.898 | 164.174832 | 0 |
| 13 | 173.52004 | 0.104286 | 0 | 289031.195 | 169.457391 | 0 |
| 14 | 173.53138 | 0.104643 | 0 | 289048.332 | 174.753942 | 0 |
| 15 | 180.58276 | 0.105 | 5202.34306 | 288856.441 | 191.891469 | 0 |

| Stage | Vapor feed kg/hr | Mixed feed kg/hr | Liquid product kg/hr | Vapor Product kg/hr |
|---|---|---|---|---|
| 1 | 0 | 0 | 12198.965 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 14548.3875 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |

TABLE 4-continued

Simulated BUOH Column Traffic and Liquid Mass Composition Profile Outputs for Example 1.

| | | | | |
|---|---|---|---|---|
| 11 | 0 | 0 | 0 | 0 |
| 12 | 0 | 0 | 0 | 0 |
| 13 | 0 | 0 | 0 | 0 |
| 14 | 0 | 0 | 0 | 0 |
| 15 | 0 | 0 | 288856.44 | 0 |

TABLE 5

Simulated Solvent Column Traffic and Liquid Mass Composition Profile Outputs for Example 1.

| Stage | Temperature C. | Pressure atm | Heat duty MJ/hr | Liquid flow kg/hr | Vapor flow kg/hr | Liquid feed kg/hr | Vapor feed kg/hr |
|---|---|---|---|---|---|---|---|
| 1 | 89.90044 | 0.986923 | 0 | 329486.759 | 70076.9632 | 347587.088 | 23545.3045 |
| 2 | 92.03997 | 0.993973 | 0 | 327948.076 | 28431.3305 | 0 | 0 |
| 3 | 93.584147 | 1.001022 | 0 | 326964.955 | 26892.6472 | 0 | 0 |
| 4 | 94.614599 | 1.008072 | 0 | 326538.175 | 25909.5257 | 0 | 0 |
| 5 | 95.232849 | 1.015121 | 0 | 326428.985 | 25482.7464 | 0 | 0 |
| 6 | 95.600773 | 1.022171 | 0 | 326528.821 | 25373.5556 | 0 | 0 |
| 7 | 95.804017 | 1.02922 | 0 | 326951.603 | 25473.3913 | 0 | 0 |
| 8 | 95.777645 | 1.036269 | 0 | 328395.495 | 25896.1722 | 0 | 0 |
| 9 | 95.536539 | 1.043319 | 0 | 333304.067 | 27340.0663 | 0 | 0 |
| 10 | 96.802423 | 1.050368 | 0 | 347274.594 | 32248.6385 | 0 | 0 |
| 11 | 104.44307 | 1.057418 | 0 | 372308.545 | 46219.1653 | 0 | 0 |
| 12 | 112.71182 | 1.064467 | 0 | 393027.462 | 71253.1165 | 0 | 0 |
| 13 | 115.45309 | 1.071517 | 0 | 399074.969 | 91972.0333 | 0 | 0 |
| 14 | 118.32958 | 1.078566 | 0 | 385748.954 | 98019.5402 | 0 | 0 |
| 15 | 180.47351 | 1.085616 | 100685.308 | 301055.429 | 84693.5252 | 0 | 0 |

| Stage | Mixed feed kg/hr | Liquid product kg/hr | Vapor Product kg/hr | 1st liquid flow kg/hr | 2nd liquid flow kg/hr |
|---|---|---|---|---|---|
| 1 | 0 | 0 | 70076.9632 | 324495.324 | 4991.4356 |
| 2 | 0 | 0 | 0 | 323518.319 | 4429.7572 |
| 3 | 0 | 0 | 0 | 323233.258 | 3731.6966 |
| 4 | 0 | 0 | 0 | 323279.874 | 3258.3013 |
| 5 | 0 | 0 | 0 | 323420.577 | 3008.4079 |
| 6 | 0 | 0 | 0 | 323680.399 | 2848.4219 |
| 7 | 0 | 0 | 0 | 324378.775 | 2572.8274 |
| 8 | 0 | 0 | 0 | 326776.18 | 1619.3156 |
| 9 | 0 | 0 | 0 | 333304.067 | 0 |
| 10 | 0 | 0 | 0 | 347274.594 | 0 |
| 11 | 0 | 0 | 0 | 372308.545 | 0 |
| 12 | 0 | 0 | 0 | 393027.462 | 0 |
| 13 | 0 | 0 | 0 | 399074.969 | 0 |
| 14 | 0 | 0 | 0 | 385748.954 | 0 |
| 15 | 0 | 301055.43 | 0 | 301055.429 | 0 |

TABLE 6

Simulated Stream Outputs for Example 2.

| | 11 | 12 | 19 | 20 | 30 | 40 | 41 | 42 |
|---|---|---|---|---|---|---|---|---|
| Temperature C. | 82.4 | 25 | 82.4 | 41.2 | 82.4 | 48.7 | 133.8 | 86.3 |
| Pressure atm | 0.99 | 2 | 0.99 | 0.99 | 0.99 | 0.1 | 1.09 | 1.05 |
| Vapor Frac | 1 | 0 | 0.177 | 0.271 | 1 | 0 | 0 | 0.061 |
| Mole Flow kmol/hr | 315.898 | 324.932 | 1102.227 | 1427.154 | 1418.125 | 192.508 | 577.519 | 1338.63 |
| Mass Flow kg/hr | 27221.551 | 28000 | 39766 | 67765.688 | 66987.56 | 14269.36 | 114991.61 | 131500 |
| Volume Flow l/hr | 8.99E+06 | 42683.8 | 5.71E+06 | 9.72E+06 | 4.11E+07 | 1.83E+04 | 1.53E+05 | 2.43E+06 |
| Enthalpy MMBtu/hr | −47.44 | −61.151 | −305.948 | −367.097 | −317.341 | −61.569 | −229.99 | −447.257 |
| Mass Flow kg/hr | | | | | | | | |
| 2-BUOH | | | 25268.47 | 25268.155 | 25268.47 | 14267.82 | 15275.043 | 18199.6 |
| OLEYLOH | | | 3.255 | 3.255 | 3.255 | 1.427 | 99716.45 | 99716.45 |
| WATER | | | 13175.94 | 13175.941 | 13175.94 | 0.115 | 0.115 | 12597.7 |

TABLE 6-continued

Simulated Stream Outputs for Example 2.

| | | | | | | | | | |
|---|---|---|---|---|---|---|---|---|---|
| N—C6 | 27221.551 | 28000 | | 28000 | 27221.55 | trace | trace | | |
| CO2 | | | 1318.336 | 1318.336 | 1318.336 | | trace | | 986.25 |
| Mass Frac | | | | | | | | | |
| 2-BUOH | | | 0.635 | 0.373 | 0.377 | 1 | 0.133 | | 0.138 |
| OLEYLOH | | | 82 PPM | 48 PPM | 49 PPM | 100 PPM | 0.867 | | 0.758 |
| WATER | | | 0.331 | 0.194 | 0.197 | 8 PPM | 1 PPM | | 0.096 |
| N—C6 | 1 | 1 | | 0.413 | 0.406 | trace | trace | | |
| CO2 | | | 0.033 | 0.019 | 0.02 | | trace | | 0.007 |

| | | 43 | 44 | 45 | 46 | 47 | 48 |
|---|---|---|---|---|---|---|---|
| | Temperature C. | 32.2 | 134.9 | 45 | 35 | 35 | 35 |
| | Pressure atm | 1.05 | 0.11 | 1.26 | 1 | 1 | 1 |
| | Vapor Frac | 0 | <0.001 | 0 | 1 | 0 | 0 |
| | Mole Flow kmol/hr | 1338.63 | 385.011 | 385.011 | 33.703 | 657.014 | 736.437 |
| | Mass Flow kg/hr | 131500 | 100722.245 | 100722.245 | 1844.077 | 50479.163 | 15442.45 |
| | Volume Flow l/hr | 156198.584 | 131997.797 | 121587.742 | 839746.3 | 71401.908 | 16212.79 |
| | Enthalpy MMBtu/hr | −466.432 | −172.269 | −191.444 | −10.26 | −167.655 | −200.897 |
| | Mass Flow kg/hr | | | | | | |
| | 2-BUOH | 18199.6 | 1007.222 | 1007.222 | 70.354 | 22343.915 | 2853.887 |
| | OLEYLOH | 99716.45 | 99715.023 | 99715.023 | trace | 3.255 | <0.001 |
| | WATER | 12597.7 | trace | trace | 33.26 | 578.356 | 12564.33 |
| | N—C6 | | trace | trace | 777.074 | 27221.551 | 1.376 |
| | CO2 | 986.25 | | | 963.39 | 332.086 | 22.86 |
| | Mass Frac | | | | | | |
| | 2-BUOH | 0.138 | 0.01 | 0.01 | 0.038 | 0.443 | 0.185 |
| | OLEYLOH | 0.758 | 0.99 | 0.99 | trace | 64 PPM | 18 PPB |
| | WATER | 0.096 | trace | trace | 0.018 | 0.011 | 0.814 |
| | N—C6 | | trace | trace | 0.421 | 0.539 | 89 PPM |
| | CO2 | 0.007 | | | 0.522 | 0.007 | 0.001 |

TABLE 7

Simulated BUOH Column Traffic and Liquid Mass Composition Profile Outputs for Example 2.

| Stage | Temperature C. | Pressure atm | Heat duty MJ/hr | Liquid flow kg/hr | Vapor flow kg/hr | Liquid feed kg/hr | Vapor feed kg/hr | Mixed feed kg/hr | Liquid product kg/hr | Vapor product kg/hr |
|---|---|---|---|---|---|---|---|---|---|---|
| 1 | 48.6552774 | 0.1 | −10636.9 | 1785.5905 | 0 | 0 | 0 | 0 | 14269.3629 | 0 |
| 2 | 63.6867369 | 0.100357 | 0 | 85.806843 | 16054.95 | 0 | 0 | 0 | 0 | 0 |
| 3 | 108.916702 | 0.100714 | 0 | 76.148465 | 14355.17 | 0 | 0 | 0 | 0 | 0 |
| 4 | 109.486331 | 0.101071 | 0 | 75.876978 | 14345.51 | 0 | 0 | 0 | 0 | 0 |
| 5 | 109.494182 | 0.101429 | 0 | 75.614794 | 14345.24 | 0 | 0 | 0 | 0 | 0 |
| 6 | 109.497968 | 0.101786 | 0 | 75.354344 | 14344.98 | 0 | 13281.352 | 0 | 0 | 0 |
| 7 | 109.501899 | 0.102143 | 0 | 101785.65 | 1063.365 | 101710.3 | 0 | 0 | 0 | 0 |
| 8 | 109.517168 | 0.1025 | 0 | 101792.3 | 1063.403 | 0 | 0 | 0 | 0 | 0 |
| 9 | 109.532411 | 0.102857 | 0 | 101798.95 | 1070.059 | 0 | 0 | 0 | 0 | 0 |
| 10 | 109.54764 | 0.103214 | 0 | 101805.59 | 1076.704 | 0 | 0 | 0 | 0 | 0 |
| 11 | 109.562858 | 0.103571 | 0 | 101812.23 | 1083.344 | 0 | 0 | 0 | 0 | 0 |
| 12 | 109.57808 | 0.103929 | 0 | 101818.86 | 1089.979 | 0 | 0 | 0 | 0 | 0 |
| 13 | 109.595037 | 0.104286 | 0 | 101825.45 | 1096.611 | 0 | 0 | 0 | 0 | 0 |
| 14 | 109.831401 | 0.104643 | 0 | 101839.12 | 1103.205 | 0 | 0 | 0 | 0 | 0 |
| 15 | 134.947659 | 0.105 | 6577.239 | 100722.25 | 1116.879 | 0 | 0 | 0 | 100722.245 | 0 |

TABLE 8

Simulated Solvent Column Traffic and Liquid Mass Composition Profile Outputs for Example 2.

| Stage | Temperature C. | Pressure atm | Heat duty MJ/hr | Liquid flow kg/hr | Vapor flow kg/hr | Liquid feed kg/hr | Vapor feed kg/hr |
|---|---|---|---|---|---|---|---|
| 1 | 82.3689722 | 0.986923 | 0 | 166694.87 | 66987.55 | 179035.7 | 2943.4325 |
| 2 | 88.4664084 | 0.993973 | 0 | 166093.99 | 51703.26 | 0 | 0 |
| 3 | 89.592452 | 1.001022 | 0 | 166174.81 | 51102.38 | 0 | 0 |

TABLE 8-continued

Simulated Solvent Column Traffic and Liquid Mass Composition Profile Outputs for Example 2.

| | | | | | | |
|---|---|---|---|---|---|---|
| 4 | 89.8809647 | 1.008072 | 0 | 166251.67 | 51183.2 | 0 | 0 |
| 5 | 90.069111 | 1.015121 | 0 | 166335.8 | 51260.06 | 0 | 0 |
| 6 | 90.2404619 | 1.022171 | 0 | 166495.41 | 51344.19 | 0 | 0 |
| 7 | 90.3737446 | 1.02922 | 0 | 167244.78 | 51503.8 | 0 | 0 |
| 8 | 90.2737243 | 1.036269 | 0 | 172619.31 | 52253.17 | 0 | 0 |
| 9 | 91.0952456 | 1.043319 | 0 | 186420.06 | 57627.7 | 0 | 0 |
| 10 | 95.3561594 | 1.050368 | 0 | 207633.68 | 71428.45 | 0 | 0 |
| 11 | 102.119063 | 1.057418 | 0 | 223920.03 | 92642.07 | 0 | 0 |
| 12 | 105.366169 | 1.064467 | 0 | 230313.89 | 108928.4 | 0 | 0 |
| 13 | 106.280325 | 1.071517 | 0 | 231792.22 | 115322.3 | 0 | 0 |
| 14 | 106.961476 | 1.078566 | 0 | 222621.51 | 116800.6 | 0 | 0 |
| 15 | 133.823958 | 1.085616 | 71302.26 | 114991.61 | 107629.9 | 0 | 0 |

| Stage | Mixed feed kg/hr | Liquid product kg/hr | Vapor product kg/hr | 1st liquid flow kg/hr | 2nd liquid flow kg/hr |
|---|---|---|---|---|---|
| 1 | 0 | 0 | 66987.5546 | 159583.165 | 7111.706 |
| 2 | 0 | 0 | 0 | 161373.554 | 4720.434 |
| 3 | 0 | 0 | 0 | 161779.908 | 4394.904 |
| 4 | 0 | 0 | 0 | 161885.572 | 4366.093 |
| 5 | 0 | 0 | 0 | 161971.728 | 4364.074 |
| 6 | 0 | 0 | 0 | 162183.657 | 4311.754 |
| 7 | 0 | 0 | 0 | 163407.616 | 3837.165 |
| 8 | 0 | 0 | 0 | 172619.311 | 0 |
| 9 | 0 | 0 | 0 | 186420.062 | 0 |
| 10 | 0 | 0 | 0 | 207633.676 | 0 |
| 11 | 0 | 0 | 0 | 223920.034 | 0 |
| 12 | 0 | 0 | 0 | 230313.889 | 0 |
| 13 | 0 | 0 | 0 | 231792.218 | 0 |
| 14 | 0 | 0 | 0 | 222621.511 | 0 |
| 15 | 0 | 114991.608 | 0 | 114991.608 | 0 |

TABLE 9

Simulated Stream Outputs for Example 3.

| | 11 | 12 | 19 | 20 | 30 | 40 | 41 | 42 |
|---|---|---|---|---|---|---|---|---|
| Temperature C. | 90.3 | 25 | 90.3 | 74 | 90.3 | 55.7 | 179.2 | 98.7 |
| Pressure atm | 0.99 | 2 | 0.99 | 0.99 | 0.99 | 0.1 | 1.09 | 1.05 |
| Vapor Frac | 1 | 0 | 0.463 | 0.419 | 1 | 0 | 0 | 0.351 |
| Mole Flow kmol/hr | 318.181 | 324.932 | 1585.039 | 1909.969 | 1903.22 | 195.464 | 1277.828 | 2678.149 |
| Mass Flow kg/hr | 27418.27 | 28000 | 40066.464 | 68066.376 | 67484.73 | 14407.858 | 301652.712 | 330000 |
| Volume Flow l/hr | 9.28E+06 | 42683.8 | 2.19E+07 | 2.26E+07 | 5.67E+07 | 18675.154 | 416016.988 | 2.74E+07 |
| Enthalpy MMBtu/hr | −47.382 | −61.151 | −401.508 | −462.658 | −415.777 | −60.597 | −512.759 | −907.197 |
| Mass Flow kg/hr | | | | | | | | |
| ETOH | | | 2564.048 | 2564.05 | 2564.048 | 131.47 | 135.888 | 1782 |
| I-BUOH | | | 12381.9 | 12381.828 | 12381.9 | 14274.638 | 15538.515 | 17820 |
| OLEYLOH | | | 15.184 | 15.184 | 15.184 | 1.441 | 285977.999 | 285978 |
| WATER | | | 24152.756 | 24152.741 | 24152.756 | 0.302 | 0.302 | 23760 |
| N—C6 | 27418.27 | 28000 | | 28000 | 27418.266 | 0.007 | 0.007 | |
| CO2 | | | 952.576 | 952.572 | 952.576 | | trace | 660 |
| Mass Frac | | | | | | | | |
| ETOH | | | 0.064 | 0.038 | 0.038 | 0.009 | 450 PPM | 0.005 |
| I-BUOH | | | 0.309 | 0.182 | 0.183 | 0.991 | 0.052 | 0.054 |
| OLEYLOH | | | 379 PPM | 223 PPM | 225 PPM | 100 PPM | 0.948 | 0.867 |
| WATER | | | 0.603 | 0.355 | 0.358 | 21 PPM | 1 PPM | 0.072 |
| N—C6 | 1 | 1 | | 0.411 | 0.406 | 485 PPB | 24 PPB | |
| CO2 | | | 0.024 | 0.014 | 0.014 | | trace | 0.002 |

| | 43 | 44 | 45 | 46 | 47 | 48 |
|---|---|---|---|---|---|---|
| Temperature C. | 32.2 | 179.9 | 45 | 35 | 35 | 35 |
| Pressure atm | 1.05 | 0.11 | 1.26 | 1 | 1 | 1 |
| Vapor Frac | 0 | 0 | 0 | 1 | 0 | 0 |
| Mole Flow kmol/hr | 2678.149 | 1082.364 | 1082.364 | 22.795 | 502.9 | 1384.274 |
| Mass Flow kg/hr | 330000 | 287244.85 | 287244.85 | 1263.391 | 39137.465 | 27665.52 |
| Volume Flow l/hr | 391079 | 393765.54 | 346651.34 | 567491.8 | 57344.707 | 28796.306 |
| Enthalpy MMBtu/hr | −991.663 | −4157.45 | −541.915 | −6.798 | −115.852 | −374.868 |
| Mass Flow kg/hr | | | | | | |
| ETOH | 1782 | 4.418 | 4.418 | 12.796 | 917.942 | 1633.312 |
| I-BUOH | 17820 | 1263.877 | 1263.877 | 22.466 | 10100.433 | 2258.929 |
| OLEYLOH | 285978 | 285976.56 | 285976.56 | trace | 15.183 | 0.001 |
| WATER | 23760 | <0.001 | <0.001 | 22.338 | 393.058 | 23737.345 |

TABLE 9-continued

Simulated Stream Outputs for Example 3.

|  |  |  |  |  |  |  |
|---|---|---|---|---|---|---|
| N—C6 |  | <0.001 | <0.001 | 577.788 | 27418.273 | 3.939 |
| CO2 | 660 |  |  | 628.004 | 292.576 | 31.993 |
| Mass Frac |  |  |  |  |  |  |
| ETOH | 0.005 | 15 PPM | 15 PPM | 0.01 | 0.023 | 0.059 |
| I-BUOH | 0.054 | 0.004 | 0.004 | 0.018 | 0.258 | 0.082 |
| OLEYLOH | 0.867 | 0.996 | 0.996 | trace | 388 PPM | 38 PPB |
| WATER | 0.072 | trace | trace | 0.018 | 0.01 | 0.858 |
| N—C6 |  | 1 PPB | 1 PPB | 0.457 | 0.701 | 142 PPM |
| CO2 | 0.002 |  |  | 0.497 | 0.007 | 0.001 |

TABLE 10

Simulated BUOH Column Traffic and Liquid Mass Composition Profile Outputs for Example 3.

| Stage | Temperature C. | Pressure atm | Heat duty MJ/hr | Liquid flow kg/hr | Vapor flow kg/hr | Liquid feed kg/hr | Vapor feed kg/hr | Mixed feed kg/hr | Liquid product kg/hr | Vapor product kg/hr |
|---|---|---|---|---|---|---|---|---|---|---|
| 1 | 55.7230656 | 0.1 | −13072.952 | 5148.01225 | 0 | 0 | 0 | 0 | 14407.8576 | 0 |
| 2 | 66.0005921 | 0.100357 | 0 | 1830.69877 | 19555.8699 | 0 | 0 | 0 | 0 | 0 |
| 3 | 157.681836 | 0.100714 | 0 | 2344.48379 | 16238.5564 | 0 | 0 | 0 | 0 | 0 |
| 4 | 168.537249 | 0.101071 | 0 | 2448.29746 | 16752.3414 | 0 | 0 | 0 | 0 | 0 |
| 5 | 169.516848 | 0.101429 | 0 | 2454.23367 | 16856.1551 | 0 | 0 | 0 | 0 | 0 |
| 6 | 169.642769 | 0.101786 | 0 | 2451.11918 | 16862.0913 | 0 | 16579.9248 | 0 | 0 | 0 |
| 7 | 169.691465 | 0.102143 | 0 | 287523.817 | 279.051976 | 285072.79 | 0 | 0 | 0 | 0 |
| 8 | 169.695336 | 0.1025 | 0 | 287529.986 | 278.962335 | 0 | 0 | 0 | 0 | 0 |
| 9 | 169.699204 | 0.102857 | 0 | 287536.151 | 285.132019 | 0 | 0 | 0 | 0 | 0 |
| 10 | 169.703074 | 0.103214 | 0 | 287542.318 | 291.29657 | 0 | 0 | 0 | 0 | 0 |
| 11 | 169.706957 | 0.103571 | 0 | 287548.512 | 297.463998 | 0 | 0 | 0 | 0 | 0 |
| 12 | 169.71089 | 0.103929 | 0 | 287554.799 | 303.657864 | 0 | 0 | 0 | 0 | 0 |
| 13 | 169.715002 | 0.104286 | 0 | 287561.407 | 309.944452 | 0 | 0 | 0 | 0 | 0 |
| 14 | 169.74111 | 0.104643 | 0 | 287597.336 | 316.552264 | 0 | 0 | 0 | 0 | 0 |
| 15 | 179.919428 | 0.105 | 7493.70774 | 287244.854 | 352.482021 | 0 | 0 | 0 | 287244.854 | 0 |

TABLE 11

Simulated Solvent Column Traffic and Liquid Mass Composition Profile Outputs for Example 3.

| Stage | Temperature C. | Pressure atm | Heat duty MJ/hr | Liquid flow kg/hr | Vapor flow kg/hr | Liquid feed kg/hr | Vapor feed kg/hr |
|---|---|---|---|---|---|---|---|
| 1 | 90.2737901 | 0.986923 | 0 | 327752.862 | 67484.7296 | 346665.91 | 22471.5596 |
| 2 | 93.0572955 | 0.993973 | 0 | 326403.278 | 26100.1266 | 0 | 0 |
| 3 | 94.3960156 | 1.001022 | 0 | 325974.85 | 24750.5432 | 0 | 0 |
| 4 | 94.8146128 | 1.008072 | 0 | 326144.402 | 24322.114 | 0 | 0 |
| 5 | 94.8676272 | 1.015121 | 0 | 326800.306 | 24491.6668 | 0 | 0 |
| 6 | 94.8184823 | 1.022171 | 0 | 327970.191 | 25147.571 | 0 | 0 |
| 7 | 94.7137098 | 1.02922 | 0 | 329966.879 | 26317.4555 | 0 | 0 |
| 8 | 94.8586927 | 1.036269 | 0 | 333728.733 | 28314.1443 | 0 | 0 |
| 9 | 96.2431649 | 1.043319 | 0 | 341275.441 | 32075.9976 | 0 | 0 |
| 10 | 100.912585 | 1.050368 | 0 | 355085.56 | 39622.7057 | 0 | 0 |
| 11 | 108.908087 | 1.057418 | 0 | 373678.684 | 53432.8253 | 0 | 0 |
| 12 | 116.020495 | 1.064467 | 0 | 389742.124 | 72025.9491 | 0 | 0 |
| 13 | 120.137323 | 1.071517 | 0 | 398745.229 | 88089.3888 | 0 | 0 |
| 14 | 123.873876 | 1.078566 | 0 | 390438.543 | 97092.4943 | 0 | 0 |
| 15 | 179.209764 | 1.085616 | 99715.9438 | 301652.735 | 88785.808 | 0 | 0 |

| Stage | Mixed feed kg/hr | Liquid product kg/hr | Vapor Product kg/hr | 1st liquid flow kg/hr | 2nd liquid flow kg/hr |
|---|---|---|---|---|---|
| 1 | 0 | 0 | 67484.73 | 324226.73 | 3526.136 |
| 2 | 0 | 0 | 0 | 323895.88 | 2507.399 |
| 3 | 0 | 0 | 0 | 324423.74 | 1551.115 |
| 4 | 0 | 0 | 0 | 325603.5 | 540.9051 |
| 5 | 0 | 0 | 0 | 326800.31 | 0 |
| 6 | 0 | 0 | 0 | 327970.19 | 0 |
| 7 | 0 | 0 | 0 | 329966.88 | 0 |
| 8 | 0 | 0 | 0 | 333728.73 | 0 |
| 9 | 0 | 0 | 0 | 341275.44 | 0 |
| 10 | 0 | 0 | 0 | 355085.56 | 0 |
| 11 | 0 | 0 | 0 | 373678.68 | 0 |
| 12 | 0 | 0 | 0 | 389742.12 | 0 |

TABLE 11-continued

Simulated Solvent Column Traffic and Liquid Mass Composition Profile Outputs for Example 3.

| | | | | | | |
|---|---|---|---|---|---|---|
| 13 | 0 | 0 | 0 | 398745.23 | 0 | |
| 14 | 0 | 0 | 0 | 390438.54 | 0 | |
| 15 | 0 | 301652.735 | 0 | 301652.74 | 0 | |

TABLE 12

Simulated Stream Outputs for Example 4.

| | 11 | 12 | 19 | 20 | 30 | 40 | 41 | 42 |
|---|---|---|---|---|---|---|---|---|
| Temperature C. | 89.9 | 25 | 89.9 | 74.8 | 89.9 | 55.1 | 180.3 | 98.3 |
| Pressure atm | 0.99 | 2 | 0.99 | 0.99 | 0.99 | 0.1 | 1.09 | 1.05 |
| Vapor Frac | 1 | 0 | 0.487 | 0.438 | 1 | 0 | <0.001 | 0.344 |
| Mole Flow kmol/hr | 318.173 | 324.932 | 1606.901 | 1931.828 | 1925.073 | 187.491 | 1264.992 | 2698.686 |
| Mass Flow kg/hr | 27417.571 | 28000 | 41033.238 | 69032.996 | 68450.81 | 13757.94 | 299691.83 | 330000 |
| Volume Flow l/hr | 9.27E+06 | 42683.8 | 2.33E+07 | 2.39E+07 | 5.73E+07 | 17822.85 | 413707.58 | 2.71E+07 |
| Enthalpy MMBtu/hr | −47.402 | −61.151 | −404.705 | −465.855 | −420.079 | −58.034 | −507.577 | −912.025 |
| Mass Flow kg/hr | | | | | | | | |
| ETOH | | | 4410.924 | 4410.829 | 4410.924 | 228.226 | 236.869 | 3284.89 |
| I-BUOH | | | 11661.322 | 11661.168 | 11661.322 | 13528.03 | 14786.134 | 17738.403 |
| OLEYLOH | | | 14.769 | 14.769 | 14.769 | 1.376 | 284668.52 | 284668.53 |
| WATER | | | 24003.591 | 24003.597 | 24003.591 | 0.299 | 0.3 | 23651.205 |
| N—C6 | 27417.571 | 28000 | | 28000 | 27417.571 | 0.009 | 0.009 | |
| CO2 | | | 942.632 | 942.633 | 942.632 | | trace | 656.978 |
| Mass Frac | | | | | | | | |
| ETOH | | | 0.107 | 0.064 | 0.064 | 0.017 | 790 PPM | 0.01 |
| I-BUOH | | | 0.284 | 0.169 | 0.17 | 0.983 | 0.049 | 0.054 |
| OLEYLOH | | | 360 PPM | 214 PPM | 216 PPM | 100 PPM | 0.95 | 0.863 |
| WATER | | | 0.585 | 0.348 | 0.351 | 22 PPM | 1 PPM | 0.072 |
| N—C6 | 1 | 1 | | 0.406 | 0.401 | 648 PPB | 31 PPB | |
| CO2 | | | 0.023 | 0.014 | 0.014 | | trace | 0.002 |

| | 43 | 44 | 45 | 46 | 47 | 48 |
|---|---|---|---|---|---|---|
| Temperature C. | 32.2 | 179.4 | 45 | 35 | 35 | 35 |
| Pressure atm | 1.05 | 0.11 | 1.26 | 1 | 1 | 1 |
| Vapor Frac | 0 | <0.001 | 0 | 1 | 0 | 0 |
| Mole Flow kmol/hr | 2698.686 | 1077.501 | 1077.501 | 22.622 | 491.379 | 1417.828 |
| Mass Flow kg/hr | 330000 | 285933.89 | 285933.89 | 1254.498 | 38142.639 | 29635.86 |
| Volume Flow l/hr | 391226.974 | 391747.47 | 345069.66 | 563074.37 | 56099.458 | 31355.832 |
| Enthalpy MMBtu/hr | −995.726 | −455.757 | −539.458 | −6.724 | −111.808 | −384.109 |
| Mass Flow kg/hr | | | | | | |
| ETOH | 3284.89 | 8.642 | 8.642 | 20.072 | 1362.903 | 3027.854 |
| I-BUOH | 17738.403 | 1258.109 | 1258.109 | 20.341 | 8709.053 | 2931.774 |
| OLEYLOH | 284668.525 | 284667.14 | 284667.14 | trace | 14.762 | 0.008 |
| WATER | 23651.205 | 0.001 | 0.001 | 21.85 | 352.687 | 23629.061 |
| N—C6 | | 0.001 | 0.001 | 574.875 | 27417.58 | 7.546 |
| CO2 | 656.978 | | | 617.361 | 285.654 | 39.618 |
| Mass Frac | | | | | | |
| ETOH | 0.01 | 30 PPM | 30 PPM | 0.016 | 0.036 | 0.102 |
| I-BUOH | 0.054 | 0.004 | 0.004 | 0.016 | 0.228 | 0.099 |
| OLEYLOH | 0.863 | 0.996 | 0.996 | trace | 387 PPM | 263 PPB |
| WATER | 0.072 | 2 PPB | 2 PPB | 0.017 | 0.009 | 0.797 |
| N—C6 | | 2 PPB | 2 PPB | 0.458 | 0.719 | 255 PPM |
| CO2 | 0.002 | | | 0.492 | 0.007 | 0.001 |

TABLE 13

Simulated BUOH Column Traffic and Liquid Mass Composition Profile Outputs for Example 4.

| Stage | Temperature C. | Pressure atm | Heat duty MJ/hr | Liquid flow kg/hr | Vapor flow kg/hr | Liquid feed kg/hr | Vapor feed kg/hr | Mixed feed kg/hr | Liquid product kg/hr | Vapor product kg/hr |
|---|---|---|---|---|---|---|---|---|---|---|
| 1 | 55.1144739 | 0.1 | −12617.119 | 5022.19711 | 0 | 0 | 0 | 0 | 13757.9351 | 0 |
| 2 | 65.8981885 | 0.10035714 | 0 | 1846.07048 | 18780.1323 | 0 | 0 | 0 | 0 | 0 |
| 3 | 158.669129 | 0.10071429 | 0 | 2397.28368 | 15604.0056 | 0 | 0 | 0 | 0 | 0 |
| 4 | 169.827438 | 0.10107143 | 0 | 2509.95284 | 16155.2188 | 0 | 0 | 0 | 0 | 0 |
| 5 | 170.864312 | 0.10142857 | 0 | 2517.10386 | 16267.888 | 0 | 0 | 0 | 0 | 0 |
| 6 | 170.999676 | 0.10178571 | 0 | 2514.16643 | 16275.039 | 0 | 16059.6263 | 0 | 0 | 0 |
| 7 | 171.0508 | 0.10214286 | 0 | 286146.277 | 212.475287 | 283632.203 | 0 | 0 | 0 | 0 |
| 8 | 171.054522 | 0.1025 | 0 | 286152.231 | 212.383637 | 0 | 0 | 0 | 0 | 0 |
| 9 | 171.058242 | 0.10285714 | 0 | 286158.181 | 218.336832 | 0 | 0 | 0 | 0 | 0 |
| 10 | 171.061964 | 0.10321429 | 0 | 286164.132 | 224.286747 | 0 | 0 | 0 | 0 | 0 |
| 11 | 171.065695 | 0.10357143 | 0 | 286170.101 | 230.237834 | 0 | 0 | 0 | 0 | 0 |
| 12 | 171.069468 | 0.10392857 | 0 | 286176.15 | 236.206967 | 0 | 0 | 0 | 0 | 0 |
| 13 | 171.073414 | 0.10428571 | 0 | 286182.519 | 242.255662 | 0 | 0 | 0 | 0 | 0 |
| 14 | 171.091794 | 0.10464286 | 0 | 286208.47 | 248.625404 | 0 | 0 | 0 | 0 | 0 |
| 15 | 179.365191 | 0.105 | 6060.6846 | 285933.894 | 274.575729 | 0 | 0 | 0 | 285933.894 | 0 |

TABLE 14

Simulated Solvent Column Traffic and Liquid Mass Composition Profile Outputs for Example 4.

| Stage | Temperature C. | Pressure atm | Heat duty MJ/hr | Liquid flow kg/hr | Vapor flow kg/hr | Liquid feed kg/hr | Vapor feed kg/hr |
|---|---|---|---|---|---|---|---|
| 1 | 89.8684731 | 0.9869233 | 0 | 326685.251 | 68450.8095 | 345571.561 | 22571.0777 |
| 2 | 92.586366 | 0.99397275 | 0 | 325426.573 | 26993.4216 | 0 | 0 |
| 3 | 93.5997789 | 1.0010222 | 0 | 325331.532 | 25734.7433 | 0 | 0 |
| 4 | 94.0635457 | 1.00807165 | 0 | 326058.842 | 25639.7023 | 0 | 0 |
| 5 | 94.087064 | 1.0151211 | 0 | 327276.724 | 26367.0123 | 0 | 0 |
| 6 | 93.9575626 | 1.02217055 | 0 | 329131.399 | 27584.8944 | 0 | 0 |
| 7 | 93.8968782 | 1.02922 | 0 | 331938.143 | 29439.5691 | 0 | 0 |
| 8 | 94.2742294 | 1.03626945 | 0 | 336223.174 | 32246.3131 | 0 | 0 |
| 9 | 95.8038722 | 1.0433189 | 0 | 342874.621 | 36531.3442 | 0 | 0 |
| 10 | 99.5397822 | 1.05036835 | 0 | 353185.732 | 43182.7908 | 0 | 0 |
| 11 | 105.840952 | 1.0574178 | 0 | 367540.526 | 53493.902 | 0 | 0 |
| 12 | 112.810559 | 1.06446725 | 0 | 382889.961 | 67848.6961 | 0 | 0 |
| 13 | 118.035575 | 1.0715167 | 0 | 394213.965 | 83198.1312 | 0 | 0 |
| 14 | 122.787497 | 1.07856615 | 0 | 387994.716 | 94522.1354 | 0 | 0 |
| 15 | 180.271665 | 1.0856156 | 101471.28 | 299691.83 | 88302.8866 | 0 | 0 |

| Stage | Mixed feed kg/hr | Liquid product kg/hr | Vapor Product kg/hr | 1st liquid flow kg/hr | 2nd liquid flow kg/hr |
|---|---|---|---|---|---|
| 1 | 0 | 0 | 68450.8095 | 323426.01 | 3259.2448 |
| 2 | 0 | 0 | 0 | 323550.22 | 1876.3573 |
| 3 | 0 | 0 | 0 | 325331.53 | 0 |
| 4 | 0 | 0 | 0 | 326058.84 | 0 |
| 5 | 0 | 0 | 0 | 327276.72 | 0 |
| 6 | 0 | 0 | 0 | 329131.4 | 0 |
| 7 | 0 | 0 | 0 | 331938.14 | 0 |
| 8 | 0 | 0 | 0 | 336223.17 | 0 |
| 9 | 0 | 0 | 0 | 342874.62 | 0 |
| 10 | 0 | 0 | 0 | 353185.73 | 0 |
| 11 | 0 | 0 | 0 | 367540.53 | 0 |
| 12 | 0 | 0 | 0 | 382889.96 | 0 |
| 13 | 0 | 0 | 0 | 394213.97 | 0 |
| 14 | 0 | 0 | 0 | 387994.72 | 0 |
| 15 | 0 | 299691.83 | 0 | 299691.83 | 0 |

What is claimed is:

1. A process comprising the steps:
   a) introducing a feed comprising:
      (i) a water-immiscible organic extractant;
      (ii) water;
      (iii) at least one isomer of butanol; and
      (iv) optionally a non-condensable gas
   into a first distillation column,
   wherein the first distillation column comprises a stripping section and optionally a rectifying section at an introduction point above the stripping section, the first distillation column having an operating temperature, $T_1$ and an operating pressure $P_1$ in the stripping section;
   wherein $T_1$ and $P_1$ are selected to produce a first bottoms stream and a first vaporous overhead stream, the first bottoms stream comprising the water-immiscible organic extractant and butanol and being substantially free of water, and the first vaporous overhead stream comprising water, butanol, optionally the extractant, and optionally the non-condensable gas;

b) introducing a water-immiscible organic entrainer to at least one appropriate process stream or vessel;

c) condensing the first vaporous overhead stream to produce a gas phase and recover a mixed condensate, wherein the mixed condensate comprises:
   (i) an organic phase comprising butanol, entrainer, and water; and
   (ii) an aqueous phase comprising water and butanol; and
wherein the mixed condensate comprises sufficient entrainer to provide phase separation of the organic and the aqueous phases;

d) introducing at least a portion of the organic phase to the first distillation column; and e) introducing at least a portion of the first bottoms stream into a second distillation column having at least a stripping section and optionally a rectifying section and operating the second distillation column to produce a second bottoms stream comprising the extractant, and a second vaporous overhead stream comprising butanol.

2. The process of claim 1 wherein the extractant is selected such that it (A) preferentially extracts butanol over water and (B) is separable from butanol by distillation; and the entrainer is selected such that it (C) has a higher vapor pressure than butanol and (D) is separable from butanol by distillation.

3. The process of claim 1, wherein the appropriate process stream or vessel is selected from the feed stream, the first vaporous overhead stream, the mixed condensate stream, the first distillation column, the decanter, and combinations thereof.

4. The process of claim 1, further comprising the step of introducing at least a portion of the aqueous phase to a fermentation vessel.

5. The process of claim 1, further comprising the step of withdrawing the bottoms stream from the second distillation column and introducing at least a portion of the withdrawn bottoms stream into a fermentation vessel.

6. The process of claim 5, further comprising the step of introducing at least a portion of the aqueous phase to a fermentation vessel.

7. The process of claim 6, further comprising the step of combining at least a portion of the withdrawn bottoms stream and at least a portion of the aqueous phase before introducing the combined stream to a fermentation vessel.

8. The process of claim 1, further comprising partially condensing the gas phase to recover at least a portion of the entrainer and optionally introducing the recovered entrainer to the mixed condensate.

9. The process of claim 8, wherein non-condensable gas is present in the feed, the gas phase further comprises the non-condensable gas, and the process further comprises the step of purging at least a portion of the gas phase comprising the non-condensable gas from the process.

10. The process of claim 9, wherein the non-condensable gas comprises carbon dioxide.

11. The process of claim 1, the process further comprises the steps of:
   g) introducing the second vaporous overhead stream into a third distillation column having at least a stripping section,
   h) operating the third distillation column to produce a third bottoms stream comprising butanol and a third vaporous overhead stream comprising the entrainer; and
   i) optionally, introducing the third vaporous overhead stream to the mixed condensate.

12. The process of claim 1, wherein the feed comprises an organic phase obtained from an extractive fermentation.

13. The process of claim 1, wherein the butanol concentration in the feed is from about 0.1 weight percent to about 40 weight percent, based on the weight of the feed.

14. The process of claim 1, wherein the entrainer comprises at least one hydrocarbon.

15. The process of claim 14, wherein the entrainer comprises at least one hydrocarbon selected from the group consisting of pentane, hexane, hexene, cyclohexane, benzene, toluene, and xylene.

16. The process of claim 1, wherein the extractant comprises at least one solvent selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides, and mixtures thereof.

17. The process of claim 16, wherein the extractant comprises at least one solvent selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof.

18. The process of claim 16, wherein the butanol comprises 1-butanol.

19. The process of claim 16, wherein the butanol comprises 2-butanol.

20. The process of claim 16, wherein the butanol comprises isobutanol.

21. The process of claim 1, wherein the feed further comprises ethanol and the second vaporous overhead stream further comprises ethanol.

22. The process of claim 1 wherein the butanol in the feed introduced into a first distillation column is produced by fermentation of corn or sugar cane.

23. The process of claim 1 further comprising a process to process heat exchange between the feed introduced to the first distillation column and the first bottoms stream.

* * * * *